(12) United States Patent
Tidmarsh

(10) Patent No.: US 9,457,059 B2
(45) Date of Patent: Oct. 4, 2016

(54) COMPOSITIONS AND METHODS FOR TREATING RENAL FAILURE

(71) Applicant: La Jolla Pharmaceutical Company, San Diego, CA (US)

(72) Inventor: George Tidmarsh, Portola Valley, CA (US)

(73) Assignee: La Jolla Pharmaceutical Company, San Diego, CA (US)

(*) Notice: Subject to any disclaimer, the term of this patent is extended or adjusted under 35 U.S.C. 154(b) by 0 days.

(21) Appl. No.: 14/263,526

(22) Filed: Apr. 28, 2014

(65) Prior Publication Data

US 2014/0329747 A1 Nov. 6, 2014

Related U.S. Application Data

(63) Continuation of application No. PCT/US2014/035511, filed on Apr. 25, 2014.

(60) Provisional application No. 61/816,578, filed on Apr. 26, 2013.

(51) Int. Cl.

| | |
|---|---|
| *A61K 38/00* | (2006.01) |
| *A61K 38/08* | (2006.01) |
| *A61K 45/06* | (2006.01) |
| *A61K 38/11* | (2006.01) |
| *A61K 31/137* | (2006.01) |
| *A61K 31/165* | (2006.01) |

(52) U.S. Cl.
CPC ........... *A61K 38/085* (2013.01); *A61K 31/137* (2013.01); *A61K 31/165* (2013.01); *A61K 38/11* (2013.01); *A61K 45/06* (2013.01)

(58) Field of Classification Search
None
See application file for complete search history.

(56) References Cited

U.S. PATENT DOCUMENTS

| 4,330,532 | A | 5/1982 | Nyeki et al. |
|---|---|---|---|
| 5,216,025 | A | 6/1993 | Gross et al. |
| 5,444,067 | A | 8/1995 | Kivlighn et al. |
| 6,592,865 | B2 | 7/2003 | Parry et al. |
| 7,666,408 | B2 | 2/2010 | Bachmann |
| 2011/0144026 | A1 | 6/2011 | Chawla |

OTHER PUBLICATIONS

Medscape (downloaded online on Jan. 2, 2015 from URL: <http://emedicine.medscape.com/article/907429-workup>).*
Bachem (downloaded online on Dec. 15, 2014 from URL: <http://shop.bachem.com/h-1705-1.html>).*
Wadei et al, Hepatorenal Syndrome: Pathophysiology and Management (Clin J Am Soc Nephrol 1: 1066-1079, 2006).*
Chemwatch (downloaded online on Mar. 5, 2015 from URL:<http://www.chemwatch.net/product/angiotensin-ii-5-l-isoleucine-acetate-salt>).*
Bachem2010 (downloaded on Sep. 22, 2015 from URL:<http://web.archive.org/web/20100730002830/http://shop.bachem.com/ep6sf/peptides-and-biochemicals/angiotensins-and-related-peptides/c4750-c4771-p2.html?sorter=sortNumber-asc>).*
Ames, R.P., et al., "Prolonged Infusions of Angiotensin Ii and Norepinephrine and Blood Pressure, Electrolyte Balance, and Aldosterone and Cortisol Secretion in Normal Man and in Cirrhosis with Ascites," J Clin Invest, 44: 1171-86 (1965).
Cohn, Jay N., et al., "Studies in Clinical Shock and Hypotension. II. Hemody-namic Effects of Norepinephrine and Angiotensin," Journal of Clin. Invest., 44(9): 1494-1504 (1965).
Daskalopoulos, G., et al., "Effects of captopril on renal function in patients with cirrhosis and ascites," J Hepatol, 4(3): 330-6 (1987).
Ginès, Pere, et al., "Hepatorenal syndrome," The Lancet, 362: 1819-27 (2003).
Harrison-Bernard, L.M.; "The renal renin-angiotensin system," Adv Physiol Educ, 33(4): 270-4 (2009).
Helmy, A., et al., "Nitric oxide mediates the reduced vasoconstrictor response to angiotensin II in patients with preascitic cirrhosis," J Hepatol, 38(1): p. 44-50 (2003).
Laragh, J.H., et al., "Angiotensin II, Norepinephrine, and Renal Transport of Electrolytes and Water in Normal Man and in Cirrhosis with Ascites," J Clin Invest, 42(7): 1179-92 (1963).
Lata, Jan, "Hepatorenal Syndrome," World Journal of Gastroenterology, 18(36): 4978-4984 (Sep. 28, 2012).
Lianos, E.A., et al., "Angiotensin-induced sodium excretion patterns in cirrhosis: role of renal prostaglandins," Kidney Int, 21(1): 70-7 (1982).
McCloy, R.M., et al., "Angiotensin-induced natriuresis in cirrhosis in the absence of endogenous aldosterone secretion," Ann Intern Med, 64(6): 1271-6 (1966).
Newby, D.E., et al., "Peripheral vascular tone in patients with cirrhosis: role of the renin-angiotensin and sympathetic nervous systems," Cardiovasc Res, 38(1): 221-8 (1998).
Page, I.H. et al., "Angiotensin," Physiol Rev, 41: 331-90 (1961).
Salerno, Francesco, et al., "Diagnosis, Prevention and Treatment of Hepatorenal Syndrome in Cirrhosis," Gut Journal, 56: 1310-1318 (2007).
Sansoe, G., et al., "Inappropriately low angiotensin II generation: a factor determining reduced kidney function and survival in patients with decompensated cirrhosis," J Hepatol, 40(3): 417-23 (2004).
Schroeder, E.T., et al. "Renal Failure in Patients with Cirrhosis of the Liver* III. Evaluation of Intrarenal Blood Flow by Para-aminohippurate Extraction and Response to Angiotensin," American Journal of of Medicine; 43: 887-896 (1967).
Ziegler, T.W., "Hepatorenal Syndrome: A Disease Mediated by the Intrarenal Action of Renin," Medical Hypotheses, 2(1): 15-21 (1976).
International Search Report and Written Opinion for PCT/US2014/035511 dated Jul. 1, 2014.
LaGrange, L.P. et al., "Effect of Intravenous Angiotensin II Infusion on Responses to Hypothalamic PVN Injection of Bicuculline," Hypertension, 42:1124-1129 (2003).
Campbell, D.J., "Do intravenous and subcutaneous angiotensin II increase blood pressure by; different mechanisms?", Clinical and Experimental Pharmacology and Physiology, vol. 40, 2013, pp. 560-570.
Cohn, J. N. et al., "Studies in Clinical Shock and Hypotension. II. Hemodynamic Effects of; Norepinephrine and Angiotensin", Journal of Clinical Investigation, vol. 44, No. 9, 1965, pp. 1494-1504.

(Continued)

Primary Examiner — Sergio Coffa
(74) Attorney, Agent, or Firm — Foley Hoag LLP

(57) ABSTRACT

The present disclosure relates to the use of angiotensin II in therapeutic methods for the treatment of renal failure, especially renal failure associated with cirrhosis.

20 Claims, No Drawings

(56) References Cited

OTHER PUBLICATIONS

Correa, T.D. "Angiotensin II in Septic Shock: Effects on Tissue Perfusion, Organ Function, and; Mitochondrial Respiration in a Porcine Model of Fecal Peritonitis", Online Laboratory; Investigations, Critical Care Medicine, vol. 42, No. 8, Aug. 2014, pp. e550-e559.
Dellinger, R.P. et al., "Surviving Sepsis Campaign: International Guidelines for Management of; Severe Sepsis and Septic Shock: 2012", Special Articles, Critical Care Medicine, vol. 41, No. 2, Feb. 2013, pp. 580-637.
Nassif, A.C. et al., "Angiotensin II in Treatment of Hypotensive States", The Journal of the; American Medical Association, vol. 183, No. 9, Mar. 2, 1963, pp. 751-754.
Thomas, V.L, "Administration of angiotensin II in refractory septic shock", Critical Care Medicine,; vol. 19, No. 8, Aug. 1991, pp. 1084-1086.
Wan, L. et al., "Angiotensin II in experimental hyperdynamic sepsis", Critical Care, vol. 13, No. 6, Nov. 30, 2009, pp. 1-10.
Yunge et al., "Angiotensin for septic shock unresponsive to noradrenaline", Archives of Disease in; Childhood, vol. 82, 2000, pp. 388-389.
Page, I.H. et al., "Angiotensin", Phvsiol Rev, vol. 41, Apr. 1961, pp. 331-390.
Chawla, L.S. et al., "Intravenous Angiotensin II for the Treatment of High-output Shock (ATHOS; trial): A Pilot Study," Critical Care, vol. 18, Issue 5, Article No. 534, published on-line Oct. 6, 2014.
del Greco, F.D. MD, et al., "Clinical Experience with Angiotensin II in the Treatment of Shock," J.A.M.A., vol. 178, No. 10, pp. 130-135, 1961.
Downing, S.E., "Effects of Angiotensin II and Norepinephrine on Ventricular Performance During Oligemic Shock," The Yale Journal of Biology and Medicine, Inc., vol. 36, pp. 407-420, 1964.
Li, T. et al., "Changes in Sensitivity of Vascular Smooth Muscle to Calcium and Its Role in the Biphasic Change in Vascular Reactivity Following Hemorrhagic Shock in Rats," Chinese Critical Care Medicine, vol. 17, No. 11, pp. 647-650, Nov. 2005.
Li, T. et al., "Changes in Sensitivity of Vascular Smooth Muscle to Calcium and Its Role in the Biphasic Change in Vascular Reactivity Following Hemorrhagic Shock in Rats," Chinese Critical Care Medicine, vol. 17, No. 11, pp. 647-650, Nov. 2005, English Abstract only.
Newby D.E. et al., "Enalapril overdose and the corrective effect of intravenous angiotensin II," Br. J. Clin Pharmacal, vol. 40, pp. 103-104, 1995.
Niu, C.Y. et al., "Lymphatic Hyporeactivity and Calcium Desensitization Following Hemorrhagic Shock," Shock, vol. 37, No. 4, pp. 415-423 (2012).
Rose, J. MD, et al., "Comparison of Effects of Angiotensin and Norepinephrine on Pulmonary Circulation, Systemic Arteries and Veins, and Systemic Vascular Capacity in the Dog," Circulation, vol. 25, pp. 247-252 (1962).
Ryding, J. et al., "Reversal of 'Refractory Septic Shock' by Infusion of Amrinone and Angiotensin II in an Anthracycline-Treated Patient," Chest, 107, 201-203 (1995).
Vaile, J.C. et al., "Angiotensin II modulates cardiovascular autonomic control in the absence of baroreflex loading," Heart, vol. 80, pp. 127-133 (1998).
Angus et al., Epidemiology of severe sepsis in the United States: Analysis of incidence, outcome, and associated costs of care. Crit Care Med 29:1303-1310 (2001).
Bagshaw et al., A Multi-Centre Evaluation of the Rifle Criteria for Early Acute Kidney Injury in Critically Ill Patients. Nephrol Dial Transplant Oct. 25 (Epub): (2007).
Basso et al., History about the discovery of the renin-angiotensin system. *Hypertension* 2001, 38(6): 1246-1249.
Goldsmith et al., Effect of a pressor infusion of angiotensin II on sympathetic activity and heartrate in normal humans. *Circ Res* 1991, 68(1 ):263-268.
Harrison-Bernard, L.M., The renal renin-angiotensin system. Adv Physiol Educ, 33(4):270-74 (2009).
Heringlake, et al., "Renal Dysfunction according to the ADQI-RIFLE system and clinical practice patterns after cardiac surgery in Germany." Minerva Anestesiol 72:645-654 (2006).
Jackson et al., "Enalapril overdose treated with angiotensin infusion," Lancet 1993, 341 (8846):703.
Kuitunen et al., "Acute renal failure after cardiac surgery: evaluation of the RIFLE classification," Ann Thorac Surg 81:542-546 (2006).
Lopes et al., Prognostic utility of RIFLE for acute renal failure in patients with sepsis. Crit Care 11:408 (2007).
Rona G:, "Catecholamine cardiotoxicity," J Mol Cell Cardiol, 17(4 ): 291-306 (1985).
Russell et al., VASST Investigators: Vasopressin versus norepinephrine infusion in patients with septic shock, N Eng J Med, 358(9):877-887 (2008).
Struthers et al., "Review of aldosterone- and angiotensin 11-induced target organ damage and prevention," Cardiovasc Res, 61(4 ):663-670 (2004).
Morelli et al., "Singer M: Effect of heart rate control with esmolol on hemodynamic and clinical outcomes in patients with septic shock: a randomized clinical trial," *JAMA* 2013, 310(16):1683-1691.
Vincent et al., The SOFA (Sepsis-related Organ Failure Assessment) score to describe organ dysfunction/failure. On behalf of the Working Group on Sepsis-Related Problems of the European Society of Intensive Care Medicine. Intensive Care Med 1996, 22(7):707-710.
Myburgh et al., "CAT Study investigators: A comparison of epinephrine and norepinephrine in critically ill patients," *Intensive Care Med* 2008, 34(12):2226-2234.
Wilson et al., "U.S. trends in CABG hospital volume: the effect of adding cardiac surgery programs," Health Aff 26:162-168, 2007.
Wray et al., "Severe septic shock unresponsive to noradrenaline," Lancet 1995, 346(8990): 1604.
Whiteley, et al., "Treatment of Hypotension in Septic Shock," The Lancet, 347(9001):622 (1996).
Uchino et al., Acute Renal Failure in Critically Ill Patients: a Multinational, Multicenter Study, JAMA 294:813-818 (2005).
Vincent, J-L, et al., "Circulatory Shock," N Engl J Med, 369:18 1726-1734 (2013).
Trilli, L.E. et al., "Lisinopril Overdose and management with Intravenous Angiotensin II," Ann Pharmacother, 28(10):1165-1168 (1994).

\* cited by examiner

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Asp Arg Val Tyr Ile His Pro Phe
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Asp Arg Val Tyr Val His Pro Phe
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3
```

```
Asp Phe Phe Phe Phe
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Val Tyr Ile His Pro Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Asn Arg Val Tyr Tyr Val His Pro Phe
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide

<400> SEQUENCE: 6

Asn Ile Ile Ile Ile Ile Ile Ile Ile Ile Ile Ile Ile
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Asn Ile Ile Ile Ile Ile Ala Ala Ala Ala Ala Ala Ala Ala
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa is diiodo Tyrosine

<400> SEQUENCE: 8

Asn Xaa Xaa Xaa Xaa Ile Ile Ile Ile Ile
1               5                   10
```

COMPOSITIONS AND METHODS FOR TREATING RENAL FAILURE

RELATED APPLICATIONS

This application is a continuation of Patent Cooperation Treaty Application Serial Number PCT/US2014/035511, filed Apr. 25, 2014, which claims the benefit of priority to U.S. Provisional Patent Application Ser. No. 61/816,578, filed Apr. 26, 2013, the contents of which are hereby incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Jul. 10, 2014, is named LJH00101_ST25.txt and is 1910 KB in size.

BACKGROUND OF THE INVENTION

Hepatorenal Syndrome (HRS) is progressive renal failure associated with liver cirrhosis or fulminant liver failure. It is a life-threatening condition in which kidney function rapidly declines resulting in >50% mortality in ≤6 months. HRS occurs in 18% of cirrhotic patients within one year of diagnosis and in 39% of patients within five years. Based on the speed of progression of renal failure, as measured by serum creatinine level, HRS is categorized into two types. Type 1 HRS is the more rapidly progressing type and is characterized by a 100% increase in serum creatinine to >2.5 mg/dL within two weeks. Less than 10% survive hospitalization, and the median survival is only two weeks. Type 2 HRS is slower progressing, with serum creatinine rising gradually. However, type 2 HRS patients can develop sudden renal failure and become diagnosed with type 1 HRS. Although HRS can occur spontaneously, other common precipitating factors are bacterial infections, gastrointestinal hemorrhage, therapeutic paracentesis, etc.

Deteriorating liver function is believed to be the underlying cause of changes in the circulation to the viscera, altering blood flow and blood vessel tone in the kidneys. The renal failure in HRS is a consequence of these changes in blood flow. The presence of elevated pressure in the portal vein (portal hypertension) in patients with liver damage is thought to result in secretion of vasodilator substances in the splanchnic circulation that causes systemic arterial underfilling. This hypotensive state triggers vasoconstriction in the kidney as a means to restore systemic blood pressure. However, the effect of this restoration is insufficient to counteract the mediators of vasodilation in circulation, leading to persistent "underfilling" of the renal circulation and worsening renal vasoconstriction, leading to renal failure.

HRS is thought to be part of a spectrum of illness associated with increased pressure in the portal vein circulation, which begins with the development of fluid in the abdomen (ascites). Ascites is a major complication associated with HRS and is exacerbated by impaired sodium excretion. The spectrum continues with diuretic-resistant ascites, where the kidneys are unable to excrete sufficient sodium to clear the fluid even with the use of diuretic medications. Most individuals with type 2 HRS have diuretic-resistant ascites before they develop deterioration in kidney function.

Liver transplantation is the only available cure for HRS; however, most patients do not live long enough to have the procedure. Currently available treatment for HRS is largely supportive and administered in an effort to bridge the patient to transplantation. Volume support with salt-poor albumin is the mainstay of treatment, as HRS patients have chronic total body sodium overload despite low serum sodium levels and hypotension. Use of vasoconstrictors, such as terlipressin or vasopressin, is thought to be effective by restoring pressure in the vasodilated splanchnic circulation. However, the adverse effects of reduced organ perfusion and marginal effect on sodium excretion limit their utility (Gines, P., et al., Hepatorenal syndrome. Lancet, 2003. 362(9398): p. 1819-27; Lata, J., Hepatorenal syndrome. World J Gastroenterol, 2012. 18(36): p. 4978-84; Salerno, F., et al., Diagnosis, prevention and treatment of hepatorenal syndrome in cirrhosis. Gut, 2007. 56(9): p. 1310-8). Therefore, there is an urgent need for new agents to improve renal function at least sufficient to help support patients prior to transplantation.

SUMMARY OF THE INVENTION

In part, this disclosure proposes the method of administering a composition comprising angiotensin II for the treatment of renal failure associated with cirrhosis. In some embodiments, prior to the administration of the composition comprising angiotensin II, a patient may have a serum creatinine level greater than 1.5 mg/dl. In addition to (or in some cases instead of) serum creatinine level greater than 1.5 mg/dl, the patient may also have a 24-hour serum creatinine clearance of less than 40 ml/min. In some embodiments, the method of treating renal failure associated with cirrhosis in a patient may comprise measuring serum creatinine level and/or 24-hour serum creatinine clearance of a patient; and if a) the measured serum creatinine level is greater than 1.5 mg/dl and/or b) the measured 24-hour serum creatinine clearance is less than 40 ml/min, then administering to the patient a composition comprising angiotensin II. In certain such embodiments, if the measured serum creatinine level is not greater than 1.5 mg/dl and/or the measured 24-hour serum creatinine clearance is not less than 40 ml/min, then the patient does not receive a composition comprising angiotensin II. The renal failure may be hepatorenal syndrome. The patient may be a human.

In some embodiments, a composition comprising angiotensin II may be administered at a rate equal to or greater than 0.032 ng/kg/min, 0.32 ng/kg/min, 1.6 ng/kg/min, or 1 ng/kg/min; or at a rate in the range of 0.5 ng/min to 100 ug/min, 0.4 to 45 ug/min or 0.12 to 19 ug/min. The concentration of angiotensin II in the composition may be at least 16 ug/ml. The composition comprising angiotensin II may be administered at a rate sufficient to achieve an increase in blood pressure of at least about 10-15 mmHg and optionally continued to administer for at least about 30 minutes thereafter. In some embodiments, the composition comprising angiotensin II may be administered at a variable rate based on mean arterial pressure in a patient, wherein the mean arterial pressure does not exceed 80 mmHg, 90 mmHg, 100 mmHg, 110 mmHg or 120 mmHg. For example, the rate of administration of the angiotensin II can be modulated manually and/or automatically in response to measurements of the patient's mean arterial pressure obtained periodically or sporadically during treatment, e.g., to maintain a mean arterial pressure at this level, or within a predetermined range (e.g., 80-110 mmHg). The composition comprising angiotensin II may be administered over a period of time of at least 8 hours; at least 24 hours; or from 8 hours to 24 hours. The composition comprising angiotensin II may be administered continuously for at least 2-6 days, such as 2-11 days, continuously for 2-6 days, or for 8 hours a day over a period of at least 2-6 days, such as 2-11 days.

In another aspect, the invention provides a method of assessing the response of a patient (such as a human) with renal failure associated with cirrhosis (such as hepatorenal syndrome) to angiotensin therapy, comprising administering to the patient an initial dose of a composition comprising angiotensin II (which may be a therapeutic dose or a sub-therapeutic dose, for example, a dose less than 1 ng/kg/min or about 1 ng/kg/min) and testing the patient for a change in a therapeutic parameter (e.g., serum creatinine level, estimated glomerular filtration rate, serum sodium level, serum potassium level, urine sodium concentration, or blood pressure). For example, the therapeutic parameter of the patient can be assessed prior to administering the initial dose and again after administering the initial dose (e.g., at least half an hour later, preferably at least one hour later and/or up to 8 hours later, preferably up to 6 hours later, such as between 1 and 6 hours after administering the initial dose). Comparing the assessment of the therapeutic parameter after administering the initial dose to the assessment made prior to administering the initial dose will indicate whether the parameter is increasing or decreasing as a result of the angiotensin therapy. Typically, a decrease in the patient's serum creatinine level, urine sodium concentration, or serum potassium level or an increase in the patient's blood pressure, serum sodium level, or estimated glomerular filtration rate is indicative of a positive response to the angiotensin therapy. In certain embodiments, where the patient exhibits a positive response to the therapy, the method further comprises administering an additional dose of angiotensin II to the patient. If a patient exhibits a negative response (e.g., an increase in the patient's serum creatinine level, urine sodium concentration, or serum potassium level or a decrease in the patient's blood pressure, serum sodium level, or estimated glomerular filtration rate), the patient will typically receive no additional doses of angiotensin therapy. If a patient exhibits no response or an insignificant response, the method may further comprise administering a higher dose of the composition than the initial dose and further testing the patient for a response to the higher dose. Alternatively, if the patient exhibits no response or an insignificant response, the patient may receive no further doses of angiotensin therapy.

In certain embodiments of the method of assessing the response, the method may further comprise, prior to administering the composition to the patient, measuring serum creatinine level and/or 24-hour serum creatinine clearance of the patient; and if a) the measured serum creatinine level is greater than 1.5 mg/dl and/or b) the measured 24-hour serum creatinine clearance is less than 40 ml/min, administering to the patient the composition. In certain such embodiments, if the measured serum creatinine level is not greater than 1.5 mg/dl and/or the measured 24-hour serum creatinine clearance is not less than 40 ml/min, then the patient does not receive a composition comprising angiotensin II.

In some embodiments, the composition comprising angiotensin II may be selected from 5-valine angiotensin II acetate, 5-valine angiotensin II amide, 5-L-isoleucine angiotensin II acetate, and 5-L-isoleucine angiotensin II amide, or a pharmaceutically acceptable salt thereof, preferably manufactured under current good manufacturing conditions (cGMP). The composition comprising angiotensin II may be suitable for parenteral administration, e.g., for injection or intravenous infusion. In some embodiments, the composition comprising angiotensin II may further include an additional pharmaceutical agent, e.g., a pharmaceutical agent useful for the treatment of the renal failure associated with cirrhosis, such as terlipressin, norepinephrine, or midodrine.

DETAILED DESCRIPTION OF THE INVENTION

Angiotensin II is a peptide hormone naturally produced by the body that regulates blood pressure via vasoconstriction and sodium reabsorption. Hemodynamic effects of angiotensin II administration have been the subject of numerous clinical studies, demonstrating significant effects on systemic and renal blood flow (Harrison-Bernard, L. M., *The renal renin-angiotensin system*. Adv Physiol Educ, 2009. 33(4): p. 270-4.). Angiotensin II is a hormone produced by the renin angiotensin aldosterone system (RAAS) that modulates blood pressure via regulation of vascular smooth muscle tone and extracellular fluid homeostasis. Angiotensin II mediates its effects on the vasculature by inducing vasoconstriction and sodium retention, and so is the target of many therapies for hypertension. In addition to its systemic effects, angiotensin II has a pronounced effect on the efferent arterioles of the kidney, maintaining glomerular filtration when blood flow is reduced. Angiotensin II also regulates sodium reabsorption in the kidney by stimulating Na+/H+ exchangers in the proximal tubule and inducing the release of aldosterone and vasopressin (Harrison-Bernard, L. M., *The renal renin-angiotensin system*. Adv Physiol Educ, 2009. 33(4): p. 270-4.).

However, a paradoxical effect of angiotensin II occurs in patients with cirrhosis and ascites. Despite increasing sodium reabsorption in normal subjects, angiotensin II induces marked natriuresis and urine output in patients with cirrhosis and ascites, while inhibition of angiotensin in these patients produces the opposite effect (i.e., reduced urine sodium and output) (Ames, R. P., et al., *Prolonged Infusions of Angiotensin Ii and Norepinephrine and Blood Pressure, Electrolyte Balance, and Aldosterone and Cortisol Secretion in Normal Man and in Cirrhosis with Ascites*. J Clin Invest, 1965. 44: p. 1171-86; Lianos, E. A., et al., *Angiotensin-induced sodium excretion patterns in cirrhosis: role of renal prostaglandins*. Kidney Int, 1982. 21(1): p. 70-7; Laragh, J. H., et al., *Angiotensin II, Norepinephrine, and Renal Transport of Electrolytes and Water in Normal Man and in Cirrhosis with Ascites*. J Clin Invest, 1963. 42(7): p. 1179-92; McCloy, R. M., et al., *Angiotensin-induced natriuresis in cirrhosis in the absence of endogenous aldosterone secretion*. Ann Intern Med, 1966. 64(6): p. 1271-6; Daskalopoulos, G., et al., *Effects of captopril on renal function in patients with cirrhosis and ascites*. J Hepatol, 1987. 4(3): p. 330-6.). The increase in urine output and sodium excretion due to angiotensin II is much more pronounced than those produced by norepinephrine (Laragh, J. H. et al.). A second study (Ames, R. P., et al.) produced similar results, with angiotensin II causing a greater increase in sodium excretion compared to norepinephrine. Furthermore, in accordance with these data, use of an angiotensin converting enzyme inhibitor (e.g., captopril) that inhibits production of angiotensin II significantly reduced both sodium excretion and urinary output (Daskalopoulos, G., et al.).

The mechanism by which the differential activity of angiotensin II affects patients with cirrhosis and ascites is unknown, although various mechanisms have been proposed. Lianos et al. have proposed that patients with cirrhosis who respond to angiotensin II with natriuresis have increased intrarenal prostaglandin production. In this model, treatment with angiotensin II causes an increase in intrarenal prostaglandin release and improvement in glomerular filtration. Sansoé et al. have proposed that these patients have inadequate production of angiotensin II despite circulating levels that are much higher than in normal individuals (Sansoe, G., et al., *Inappropriately low angiotensin II generation: a factor determining reduced kidney function and survival in patients with decompensated cirrhosis*. J Hepatol, 2004. 40(3): p. 417-23.). Coupled with findings from Newby et al. demonstrating that cirrhotic patients have reduced responsiveness to angiotensin II (Newby, D. E., et al., *Peripheral vascular tone in patients with cirrhosis: role of the renin-angiotensin and sympathetic nervous systems*. Cardiovasc Res, 1998. 38(1): p. 221-8.), it is possible that these patients have a relative deficiency of angiotensin II and reduced glomerular filtration is the result of generalized vasodilation caused by this deficiency. The increased vasodilation has been attributed to increased nitric oxide (NO) synthesis (Helmy, A., et al., *Nitric oxide mediates the reduced vasoconstrictor response to angiotensin II in patients with preascitic cirrhosis*. J Hepatol, 2003. 38(1): p. 44-50.). While the exact mechanism of angiotensin II-induced sodium excretion has not been identified, plausible hypotheses exist.

Even though it was shown that angiotensin II induces marked natriuresis and urine output in the patients with cirrhosis and ascites, none of the patients included in these studies exhibited renal failure. As current vasoconstrictor therapy for HRS is limited in its ability to correct sodium dysregulation, angiotensin II may provide a significant therapeutic advantage, since its use in patients with cirrhosis and ascites has been well-tolerated.

In part, this disclosure demonstrates that a composition including angiotensin II may be used to treat hepatorenal syndrome (HRS). The treatment is not limited to HRS and may include any renal failure associated with cirrhosis or fulminant liver failure. It will be understood by those of skill in the art that this method may include treatment of other diseases where a patient may benefit from the paradoxical effect of angiotensin II as described above, i.e., marked natriuresis and/or urine output. In some embodiments, HRS may be of type I or type II. Renal failure itself may be associated with diseases such as any type of cirrhosis (regardless of the cause), severe alcoholic and/or non-alcoholic hepatitis, fulminant hepatic failure, any infection and/or injury causing deterioration in liver function, bleeding in the gastrointestinal tract, portal hypertension or elevated pressures in portal veins, nephrotic syndrome, ascites, infection of ascites fluid, complications of liver disease including removal of large volumes of ascitic fluid, overuse of diuretic medications, etc. Other causes of ascites that may result in renal failure include heart failure, hepatic venous occlusion such as Budd-Chiari syndrome or veno-occlusive disease, constrictive pericarditis, Kwashiorkor (childhood protein-energy malnutrition), cancer (primary peritoneal carcinomatosis and metastasis), infection such as tuberculosis or spontaneous bacterial peritonitis (SBP), pancreatitis, serositis, hereditary angioedema, Meigs syndrome, vasculitis, hypothyroidism, renal dialysis, peritoneum mesothelioma. Causes of cirrhosis that may result in renal failure may include alcoholic liver disease, non-alcoholic steatohepatitis, hepatitis C, hepatitis B, primary biliary cirrhosis, primary sclerosing cholangitis, autoimmune hepatitis, hereditary hemochromatosis, Wilson's disease, alpha 1-antitrypsin deficiency, cardiac cirrhosis, galactosemia, glycogen storage disease type IV, cystic fibrosis, hepatotoxic drugs or toxins, lysosomal acid lipase deficiency, etc.

Diagnostic Criteria

Several diagnostic criteria, individually or in combination, may be used to determine if a patient is suffering from HRS or if the composition including angiotensin II may be therapeutic to a particular patient. The diagnostic criterion for HRS is serum creatinine level of greater than 1.5 mg/dl. Patients with renal failure and cirrhosis that meet one or more of the following criteria may also be candidates for angiotensin therapy. For example, patients having chronic or acute liver disease with advanced hepatic failure and/or portal hypertension; cirrhosis with ascites; serum creatinine level of greater than 1.5 mg/dl and/or 24-hour creatinine clearance of less than 40 ml/minute; no improvement of serum creatinine (decrease to a level of less than or equal to 1.5 mg/dl) after at least two days of diuretic withdrawal and volume expansion with albumin where the recommended dose of albumin may be 1 g/kg of body weight per day up to a maximum of 100 g/day; no sustained improvement in renal function defined as a decrease in serum creatinine to less than 1.5 mg/dL or increase in creatinine clearance to 40 mL/min or more following diuretic withdrawal and expansion of plasma volume with 1.5 L of isotonic saline; absence of shock, ongoing bacterial infection, and current or recent treatment with nephrotoxic drugs; absence of gastrointestinal fluid losses (repeated vomiting or intense diarrhea) or renal fluid losses; proteinuria of less than 500 mg/dL and no ultrasonographic evidence of obstructive uropathy or parenchymal renal disease; absence of parenchymal kidney disease as indicated by proteinuria greater than 500 mg/day, microhematuria (greater than 50 red blood cells per high power field), and/or abnormal renal ultrasonography; urine volume of less than 500 ml/day; urine sodium of less than 10 mEq/L; urine osmolarity may be greater than plasma osmolarity; urine red blood cells may be less than 50 per high power field, etc. may benefit from the angiotensin therapy.

Angiotensin II Therapeutics

The angiotensin II therapeutic that may be used for in the compositions and methods of this disclosure may be Asp-Arg-Val-Tyr-Ile-His-Pro-Phe [SEQ ID NO: 1] also called 5-isoleucine angiotensin II. SEQ ID NO: 1 is an octa-peptide naturally present in humans and other species, such as equines, hogs, etc. The $5^{th}$ isoleucine may be substituted by valine to result in 5-valine angiotensin II, Asp-Arg-Val-Tyr-Val-His-Pro-Phe [SEQ ID NO: 2]. Other angiotensin II analogues such as [$Asn^1$-$Phe^4$]-angiotensin II [SEQ ID NO: 3], hexapeptide Val-Tyr-Ile-His-Pro-Phe [SEQ ID NO: 4], nonapeptide Asn-Arg-Val-Tyr-Tyr-Val-His-Pro-Phe [SEQ ID NO: 5], [$Asn^1$-$Ileu^5$-$Ileu^8$]-angiotensin II [SEQ ID NO: 6], [$Asn^1$-$Ileu^5$-$Ala^8$]-angiotensin II [SEQ ID NO: 7], and [$Asn^1$-diiodo$Tyr^4$-$Ileu^5$]-angiotensin II [SEQ ID NO: 8] may also be used. The term "angiotensin II", without further specificity, is intended to refer to any of these various forms, as well as combinations thereof.

The sequence of angiotensin II used in the compositions and methods disclosed herein may be homologous to the sequences of angiotensin II described above. In certain embodiments, the invention includes isolated or recombinant amino acid sequences that are at least 80%, 85%, 90%, 95%, 97%, 98%, 99% or 100% identical to SEQ ID NO: 1, 2, 3, 4, 5, 6, 7, and/or 8. Any such variant sequences may be used in place of an angiotensin II as described in the preceding paragraph.

In some embodiments, the angiotensin II included in the composition used for the treatment may be selected from 5-valine angiotensin II acetate, 5-valine angiotensin II amide, 5-L-isoleucine angiotensin II acetate, and 5-L-isoleucine angiotensin II amide, or a pharmaceutically acceptable salt thereof, preferably manufactured under current good manufacturing conditions (cGMP). In some embodiments, the composition may include different forms of angiotensin II in different percentages, e.g., a mixture of hexapeptide and nonapeptide angiotensin.

Similarly, an angiotensin II therapeutic may be used as any suitable salt, deprotected form, acetylated form, deacetylated form, and/or prodrug form of the above-mentioned peptides, including pegylated forms of the peptides or conjugates as disclosed in US Patent Publication 2011/0081371. The term "prodrug" refers to any precursor compound which is able to generate or to release the above-mentioned peptide under physiological conditions. Such prodrugs may be larger peptides which are selectively cleaved in order to form the peptide of the invention. For example, in some embodiments, the prodrug may be angiotensin I or its homologues that may result in angiotensin II by the action of certain endogenous or exogenous enzymes. Further prodrugs include peptides with protected amino acids, e.g., having protecting groups at one or more carboxylic acid and/or amino groups. Suitable protecting groups for amino groups are the benzyloxycarbonyl, t-butyloxycarbonyl (BOC), formyl, and acetyl or acyl group. Suitable protecting groups for the carboxylic acid group are esters such as benzyl esters or t-butyl esters. The present invention also contemplates the use of angiotensin II and/or precursor peptides having amino acid substitutions, deletions, additions, the substitutions and additions including the standard D and L amino acids and modified amino acids, such as, for example, amidated and acetylated amino acids, wherein the therapeutic activity of the base peptide sequence is maintained at a pharmacologically useful level.

Doses of the Therapeutically Effective Substance

The term "pharmaceutically effective amount" or "therapeutically effective amount" refers to an amount of the composition or therapeutic agent, such as angiotensin II, effective to treat renal failure in a patient, e.g., improving renal function, and/or effecting a beneficial and/or desirable alteration in the general health of a patient suffering from a disease (e.g., renal failure). The skilled worker will recognize that as used herein, the term "treating" or "treatment" includes reversing, reducing, or arresting the symptoms, clinical signs, and underlying pathology of a condition in a manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease or its symptoms, stabilized (i.e., not worsening) state of disease or its symptoms, preventing spread of disease or its symptoms, delay or slowing of disease or its symptoms' progression, amelioration or palliation of the disease state or its symptoms, and remission (whether partial or total), whether detectable or undetectable. "Treatment" can also mean prolonging survival as compared to expected survival if not receiving treatment. A "pharmaceutically effective amount" or "therapeutically effective amount" also refers to the amount required to improve the clinical symptoms of a patient. The therapeutic methods or methods of treating renal failure described herein are not to be interpreted or otherwise limited to "curing" renal failure or the disease causing the renal failure. When applied to an individual active ingredient, administered alone, the term refers to that ingredient alone. When applied to a combination, the term refers to combined amounts of the active ingredients that result in the therapeutic effect, whether administered in combination, serially or simultaneously. Unless otherwise specified, it is to be understood that each embodiment of the invention may be used alone or in combination with any one or more other embodiments of the invention.

In some embodiments, the total amount of a therapeutically effective substance (e.g., angiotensin II) in a composition to be injected in a patient is one that is suitable for that patient. One of skill in the art would appreciate that different individuals may require different total amounts of the angiotensin therapeutic. In some embodiments, the amount of the angiotensin therapeutic is a pharmaceutically effective amount. The skilled worker would be able to determine the amount of the angiotensin therapeutic in a composition needed to treat a patient based on factors such as, for example, the age, weight, and physical condition of the patient. The concentration of the angiotensin therapeutic (e.g., angiotensin II) depends in part on its solubility in the intravenous administration solution and the volume of fluid that can be administered. For example, the rate of administration of the angiotensin therapeutic (e.g. angiotensin II) may be from about 0.032 ng/kg/min to about 100 ug/kg/min in the injectable composition. In some embodiments, the rate of administration of the angiotensin therapeutic may be from about 0.4 to about 45 ug/min, from about 0.12 to about 19 ug/min, from about 3.8 to about 33.8 ug/min, from about 0.16 to about 2.6 ug/min, etc. In particular embodiments, the rate of administration of the angiotensin therapeutic may be about 0.032 ng/kg/min, about 0.1 ng/kg/min, about 0.32 ng/kg/min, about 1 ng/kg/min, about 1.6 ng/kg/min, about 2 ng/kg/min, about 3 ng/kg/min, about 4 ng/kg/min, about 5 ng/kg/min, about 6 ng/kg/min, about 7 ng/kg/min, about 8 ng/kg/min, about 9 ng/kg/min, about 10 ng/kg/min, about 15 ng/kg/min, about 20 ng/kg/min, about 25 ng/kg/min, about 30 ng/kg/min, about 40 ng/kg/min, about 50 ng/kg/min, about 60 ng/kg/min, about 70 ng/kg/min, about 80 ng/kg/min, about 90 ng/kg/min, about 100 ng/kg/min, about 200 ng/kg/min, about 300 ng/kg/min, about 400 ng/kg/min, about 500 ng/kg/min, about 600 ng/kg/min, about 700 ng/kg/min, about 800 ng/kg/min, about 900 ng/kg/min, about 1 ug/kg/min, about 1.1 ug/kg/min, about 1.2 ug/kg/min, about 1.3 ug/kg/min, about 1.4 ug/kg/min, about 1.5 ug/kg/min, about 1.5 ug/kg/min, about 1.6 ug/kg/min, about 1.7 ug/kg/min, about 1.8 ug/kg/min, about 1.9 ug/kg/min, about 2 ug/kg/min, about 2.1 ug/kg/min, about 2.2 ug/kg/min, about 2.3 ug/kg/min, about 2.4 ug/kg/min, about 2.5 ug/kg/min, about 2.6 ug/kg/min, about 2.7 ug/kg/min, about 2.8 ug/kg/min, about 2.9 ug/kg/min, about 3.0 ug/kg/min, about 3.1 ug/kg/min, about 3.2 ug/kg/min, about 3.3 ug/kg/min, about 3.4 ug/kg/min, about 3.5 ug/kg/min, about 3.6 ug/kg/min, about 3.7 ug/kg/min, about 3.8 ug/kg/min, about 3.9 ug/kg/min, about 4.0 ug/kg/min, about 4.1 ug/kg/min, about 4.2 ug/kg/min, about 4.3 ug/kg/min, about 4.4 ug/kg/min, about 4.5 ug/kg/min, about 4.6 ug/kg/min, about 4.7 ug/kg/min, about 4.8 ug/kg/min, about 4.9 ug/kg/min, about 5.0 ug/kg/min, about 6 ug/kg/min, about 7 ug/kg/min, about 8 ug/kg/min, about 9 ug/kg/min, about 10 ug/kg/min, about 11 ug/kg/min, about 12 ug/kg/min, about 13 ug/kg/min, about 14 ug/kg/min, about 15 ug/kg/min, about 16 ug/kg/min, about 17 ug/kg/min, about 18 ug/kg/min, about 19 ug/kg/min, about 20 ug/kg/min, about 25 ug/kg/min, about 30 ug/kg/min, about 31 ug/kg/min, about 32 ug/kg/min, about 33 ug/kg/min, about 33.8 ug/kg/min, about 34 ug/kg/min, about 35 ug/kg/min, about 40 ug/kg/min, about 45 ug/kg/min, about 50 ug/kg/min, about 55 ug/kg/min, about 60 ug/kg/min, about 65 ug/kg/min, about 70 ug/kg/min, about 75 ug/kg/min, about 80 ug/kg/min, about 85 ug/kg/min, about 90 ug/kg/min, about 95 ug/kg/min, about 100 ug/kg/min, etc.

The concentration of the angiotensin therapeutic (e.g., angiotensin II) in the composition administered can be at least 16 ug/ml. In some embodiments, the concentration of the angiotensin therapeutic may be about 1.0 ug/ml, about 2.0 ug/ml, about 3.0 ug/ml, about 4.0 ug/ml, about 5.0 ug/ml, about 6.0 ug/ml, about 7.0 ug/ml, about 8.0 ug/ml, about 9.0 ug/ml, about 10.0 ug/ml, about 11.0 ug/ml, about 12.0 ug/ml, about 13.0 ug/ml, about 14.0 ug/ml, about 15.0 ug/ml, etc. In general, angiotensin II increases blood pressure, and patients with cirrhosis (who are hypotensive) may require larger doses to exhibit pressor responses similar to those observed in normal subjects. The composition including the angiotensin therapeutic (e.g., angiotensin II) can be administered at a rate sufficient to achieve an increase in blood pressure of at least about 10-15 mmHg and optionally for at least angiotensin therapeutic administered may be varied in response to changes in other physiological parameters such as renal vascular resistance, renal blood flow, filtration fractions, mean arterial pressure, etc. For example, the rate of administration of the angiotensin therapeutic may start from about 0.5 ng/kg/min to about 10 ng/kg/min and is increased based on the mean arterial pressure (MAP). In some embodiments, the rate of administration may be increased such that the MAP does not exceed about 70 mmHg, about 80 mmHg, about 90 mmHg, about 100 mmHg, about 110 mmHg, etc. For example, a patient may be coupled to a monitor that provides continuous, periodic, or occasional measurements of MAP during some or all of the course of treatment. The rate of administration may be modulated manually (e.g., by a physician or nurse) or automatically (e.g., by a medical device capable of modulating delivery of the composition in response to MAP values received from the monitor) to maintain the patient's MAP within a desired range (e.g., 80-110 mmHg) or below a desired threshold, e.g., as set forth above.

The composition including the angiotensin therapeutic may be administered over a period of time selected from at least 8 hours; at least 24 hours; and from 8 hours to 24 hours. The composition including the angiotensin therapeutic may be administered continuously for at least 2-6 days, such as 2-11 days, continuously for 2-6 days, for 8 hours a day over a period of at least 2-6 days, such as 2-11 days. A weaning period (from several hours to several days) may be beneficial after prolonged infusion.

The composition including the angiotensin therapeutic may further include one or more additional pharmaceutical agent. For example, angiotensin II may be administered with albumin since expansion of the volume of the plasma with albumin given intravenously has shown to improve renal function in patients with hepatorenal syndrome. The quantity of the additional pharmaceutical agent administered may vary depending on the cumulative therapeutic effect of the treatment including the angiotensin therapeutic and the additional pharmaceutical agent. For example, the quantity of albumin administered may be 1 gram of albumin per kilogram of body weight given intravenously on the first day, followed by 20 to 40 grams daily. Yet other additional pharmaceutical agents may be any one or more of midodrine, octreotide, somatostatin, vasopressin analogue omnipressin, terlipressin, pentoxifylline, acetylcysteine, norepinephrine, misoprostol, etc. In some embodiments, other natriuretic peptides may also be used in combination with the angiotensin therapeutic to remedy the impairment of sodium excretion associated with diseases discussed above. For example, natriuretic peptides may include any type of atrial natriuretic peptide (ANP), brain natriuretic peptide (BNP), C-type natriuretic peptide (CNP), and/or dendroaspis natriuretic peptide, etc. Several diuretic compounds may be used in combination with the angiotensin therapeutic to induce urine output. For example any one or more of the xanthines such as caffeine, theophylline, theobromine; thiazides such as bendroflumethiazide, hydrochlorothiazide; potassium-sparing diuretics such as amiloride, spironolactone, triamterene, potassium canrenoate; osmotic diuretics such as glucose (especially in uncontrolled diabetes), mannitol; loop diuretics such as bumetanide, ethacrynic acid, furosemide, torsemide; carbonic anhydrase inhibitors such as acetazolamide, dorzolamide; Na—H exchanger antagonists such as dopamine; aquaretics such as goldenrod, juniper; arginine vasopressin receptor 2 antagonists such as amphotericin B, lithium citrate; acidifying salts such as $CaCl_2$, $NH_4Cl$; ethanol, water, etc. may be used in combination with the angiotensin therapeutic to treat the patient. The list of additional pharmaceutical agents described above is merely illustrative and may include any other pharmaceutical agents that may be useful for the treatment of renal failure associated with any of the diseases and conditions discussed above.

Excipients

The pharmaceutical compositions of the present invention may also contain diluents, fillers, salts, buffers, stabilizers, solubilizers, and other materials well known in the art. The term "pharmaceutically acceptable carrier" refers to a non-toxic carrier that may be administered to a patient, together with a therapeutically effective substance (such as angiotensin II) of this invention, and which does not destroy the pharmacological activity of the therapeutically effective substance. The term "pharmaceutically acceptable" means a non-toxic material that does not interfere with the effectiveness of the biological activity of the active ingredient(s). The characteristics of the carrier will depend on the route of administration. The term "excipient" refers to an additive in a formulation or composition that is not a pharmaceutically active ingredient.

One of skill in the art would appreciate that the choice of any one excipient may influence the choice of any other excipient. For example, the choice of a particular excipient may preclude the use of one or more additional excipients because the combination of excipients would produce undesirable effects. One of skill in the art would be able to empirically determine which excipients, if any, to include in the compositions of the invention. Excipients of the invention may include, but are not limited to, co-solvents, solubilizing agents, buffers, pH adjusting agents, bulking agents, surfactants, encapsulating agents, tonicity-adjusting agents, stabilizing agents, protectants, and viscosity modifiers. In some embodiments, it may be beneficial to include a pharmaceutically acceptable carrier in the compositions of the invention.

Solubilizing Agents

In some embodiments, it may be beneficial to include a solubilizing agent in the compositions of the invention. Solubilizing agents may be useful for increasing the solubility of any of the components of the formulation or composition, including a therapeutically effective substance (e.g., angiotensin II) or an excipient. The solubilizing agents described herein are not intended to constitute an exhaustive list, but are provided merely as exemplary solubilizing agents that may be used in the compositions of the invention. In certain embodiments, solubilizing agents include, but are not limited to, ethyl alcohol, tert-butyl alcohol, polyethylene glycol, glycerol, methylparaben, propylparaben, polyethylene glycol, polyvinyl pyrrolidone, and any pharmaceutically acceptable salts and/or combinations thereof.

pH-Adjusting Agents

In some embodiments, it may be beneficial to adjust the pH of the compositions by including a pH-adjusting agent in the compositions of the invention. Modifying the pH of a formulation or composition may have beneficial effects on, for example, the stability or solubility of a therapeutically effective substance, or may be useful in making a formulation or composition suitable for parenteral administration. pH-adjusting agents are well known in the art. Accordingly, the pH-adjusting agents described herein are not intended to constitute an exhaustive list, but are provided merely as exemplary pH-adjusting agents that may be used in the compositions of the invention. pH-adjusting agents may include, for example, acids and bases. In some embodiments, a pH-adjusting agent includes, but is not limited to, acetic acid, hydrochloric acid, phosphoric acid, sodium hydroxide, sodium carbonate, and combinations thereof.

The pH of the compositions of the invention may be any pH that provides desirable properties for the formulation or composition. Desirable properties may include, for example, therapeutically effective substance (e.g., angiotensin II) stability, increased therapeutically effective substance retention as compared to compositions at other pHs, and improved filtration efficiency. In some embodiments, the pH of the compositions of the invention may be from about 3.0 to about 9.0, e.g., from about 5.0 to about 7.0. In particular embodiments, the pH of the compositions of the invention may be 5.5±0.1, 5.6±0.1, 5.7±0.1, 5.8±0.1, 5.9±0.1, 6.0±0.1, 6.1±0.1, 6.2±0.1, 6.3±0.1, 6.4±0.1, or 6.5±0.1.

Buffers

In some embodiments, it may be beneficial to buffer the pH by including one or more buffers in the compositions. In certain embodiments, a buffer may have a pKa of, for example, about 5.5, about 6.0, or about 6.5. One of skill in the art would appreciate that an appropriate buffer may be chosen for inclusion in compositions of the invention based on its pKa and other properties. Buffers are well known in the art. Accordingly, the buffers described herein are not intended to constitute an exhaustive list, but are provided merely as exemplary buffers that may be used in the compositions of the invention. In certain embodiments, a buffer may include one or more of the following: Tris, Tris HCl, potassium phosphate, sodium phosphate, sodium citrate, sodium ascorbate, combinations of sodium and potassium phosphate, Tris/Tris HCl, sodium bicarbonate, arginine phosphate, arginine hydrochloride, histidine hydrochloride, cacodylate, succinate, 2-(N-morpholino)ethanesulfonic acid (MES), maleate, bis-tris, phosphate, carbonate, and any pharmaceutically acceptable salts and/or combinations thereof.

Surfactants

In some embodiments, it may be beneficial to include a surfactant in the compositions of the invention. Surfactants, in general, reduce the surface tension of a liquid composition. This may provide beneficial properties such as improved ease of filtration. Surfactants also may act as emulsifying agents and/or solubilizing agents. Surfactants are well known in the art. Accordingly, the surfactants described herein are not intended to constitute an exhaustive list, but are provided merely as exemplary surfactants that may be used in the compositions of the invention. Surfactants that may be included include, but are not limited to, sorbitan esters such as polysorbates (e.g., polysorbate 20 and polysorbate 80), lipopolysaccharides, polyethylene glycols (e.g., PEG 400 and PEG 3000), poloxamers (i.e., pluronics), ethylene oxides and polyethylene oxides (e.g., Triton X-100), saponins, phospholipids (e.g., lecithin), and combinations thereof.

Tonicity-Adjusting Agents

In some embodiments, it may be beneficial to include a tonicity-adjusting agent in the compositions of the invention. The tonicity of a liquid composition is an important consideration when administering the composition to a patient, for example, by parenteral administration. Tonicity-adjusting agents, thus, may be used to help make a formulation or composition suitable for administration. Tonicity-adjusting agents are well known in the art. Accordingly, the tonicity-adjusting agents described herein are not intended to constitute an exhaustive list, but are provided merely as exemplary tonicity-adjusting agents that may be used in the compositions of the invention. Tonicity-adjusting agents may be ionic or non-ionic and include, but are not limited to, inorganic salts, amino acids, carbohydrates, sugars, sugar alcohols, and carbohydrates. Exemplary inorganic salts may include sodium chloride, potassium chloride, sodium sulfate, and potassium sulfate. An exemplary amino acid is glycine. Exemplary sugars may include sugar alcohols such as glycerol, propylene glycol, glucose, sucrose, lactose, and mannitol.

Stabilizing Agents

In some embodiments, it may be beneficial to include a stabilizing agent in the compositions of the invention. Stabilizing agents help increase the stability of a therapeutically effective substance in compositions of the invention. This may occur by, for example, reducing degradation or preventing aggregation of a therapeutically effective substance. Without wishing to be bound by theory, mechanisms for enhancing stability may include sequestration of the therapeutically effective substance from a solvent or inhibiting free radical oxidation of the anthracycline compound. Stabilizing agents are well known in the art. Accordingly, the stabilizing agents described herein are not intended to constitute an exhaustive list, but are provided merely as exemplary stabilizing agents that may be used in the compositions of the invention. Stabilizing agents may include, but are not limited to, emulsifiers and surfactants.

Routes of Delivery

The compositions of the invention can be administered in a variety of conventional ways. In some embodiments, the compositions of the invention are suitable for parenteral administration. These compositions may be administered, for example, intraperitoneally, intravenously, intrarenally, or intrathecally. In some embodiments, the compositions of the invention are injected intravenously. One of skill in the art would appreciate that a method of administering a therapeutically effective substance formulation or composition of the invention would depend on factors such as the age, weight, and physical condition of the patient being treated, and the disease or condition being treated. The skilled worker would, thus, be able to select a method of administration optimal for a patient on a case-by-case basis.

Unless otherwise defined herein, scientific and technical terms used in this application shall have the meanings that are commonly understood by those of ordinary skill in the art. Generally, nomenclature and techniques relating to chemistry, molecular biology, cell and cancer biology, immunology, microbiology, pharmacology, and protein and nucleic acid chemistry, described herein, are those well known and commonly used in the art.

Throughout this specification, the word "comprise" or variations such as "comprises" or "comprising" will be understood to imply the inclusion of a stated integer (or components) or group of integers (or components), but not the exclusion of any other integer (or components) or group of integers (or components). The singular forms "a," "an," and "the" include the plurals unless the context clearly dictates otherwise. The term "including" is used to mean "including but not limited to." "Including" and "including but not limited to" are used interchangeably. The terms "patient" and "individual" are used interchangeably and refer to either a human or a non-human animal. These terms include mammals such as humans, primates, livestock animals (e.g., bovines, porcines), companion animals (e.g., canines, felines) and rodents (e.g., mice, rabbits and rats).

"About" and "approximately" shall generally mean an acceptable degree of error for the quantity measured given the nature or precision of the measurements. Typically, exemplary degrees of error are within 20%, preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

Incorporation by Reference

All publications and patents mentioned herein are hereby incorporated by reference in their entirety as if each individual publication or patent was specifically and individually indicated to be incorporated by reference. In case of conflict, the present specification, including its specific definitions, will control. While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

I claim:

1. A method of treating renal failure associated with cirrhosis in a patient in need thereof, comprising: administering to the patient angiotensin II at an initial rate of 0.5 ng/kg/min to 10 ng/kg/min; measuring the mean arterial pressure of the patient; and modulating the rate of administration of angiotensin II within the range of 0.5 ng/min to 100 μg/min to maintain the mean arterial pressure of the patient within 80 mm Hg and 110 mm Hg over a period of time of at least 8 hours, wherein: the patient has renal failure associated with cirrhosis; the angiotensin II is 5-valine angiotensin II, 5-valine angiotensin II amide, 5-L-isoleucine angiotensin II, 5-L-isoleucine angiotensin II amide, or a pharmaceutically acceptable salt of any one of the foregoing.

2. The method of claim 1, wherein, prior to administration, the patient has a serum creatinine level greater than 1.5 mg/dl.

3. The method of claim 1, wherein, prior to administration, the patient has a 24-hour serum creatinine clearance of less than 40 ml/min.

4. A method of treating renal failure associated with cirrhosis in a patient in need thereof, comprising: measuring serum creatinine level and/or 24-hour serum creatinine clearance of a patient; and if a) the measured serum creatinine level is greater than 1.5 mg/dl or b) the measured 24-hour serum creatinine clearance is less than 40 ml/min, administering to the patient angiotensin II at a rate of 0.5 ng/kg/min to 10 ng/kg/min over a period of time of at least 8 hours, wherein the angiotensin II is 5-valine angiotensin II, 5-valine angiotensin II amide, 5-L-isoleucine angiotensin II, 5-L-isoleucine angiotensin II amide, or a pharmaceutically acceptable salt of any one of the foregoing.

5. The method of claim 1, wherein the renal failure is hepatorenal syndrome.

6. The method of claim 1, wherein the patient is a human.

7. The method of claim 6, wherein administering angiotensin II comprises administering a composition comprising angiotensin II, and the composition has a concentration of the angiotensin II of at least 16 µg/ml.

8. The method of claim 6, comprising administering the angiotensin II at a rate sufficient to achieve an increase in blood pressure of at least about 10-15 mmHg and optionally continuing to administer for at least about 30 minutes thereafter.

9. The method of claim 6, comprising administering the angiotensin II at a variable rate based on mean arterial pressure in the patient, wherein the mean arterial pressure does not exceed 80 mmHg, 90 mmHg, 100 mmHg, 110 mmHg or 120 mmHg.

10. The method of claim 1, comprising administering the angiotensin II over a period of time selected from at least 24 hours and from 8 hours to 24 hours.

11. The method of claim 1, comprising administering the angiotensin II continuously for 2-11 days.

12. The method of claim 11, comprising administering the angiotensin II continuously for 2-6 days.

13. The method of claim 1, wherein the angiotensin II is administered for 8 hours a day over a period of 2-11 days.

14. The method of claim 1, wherein the mean arterial pressure of the patient is measured and the rate of administration of angiotensin II is modulated at least half an hour after administering the initial dose.

15. The method of claim 1, wherein the mean arterial pressure of the patient is measured and the rate of administration of angiotensin II is modulated less than eight hours after administering the initial dose.

16. The method of claim 1, wherein the angiotensin II is administered in a composition suitable for parenteral administration.

17. The method of claim 16, wherein the parenteral administration is injection or intravenous infusion.

18. The method of claim 1, wherein administering angiotensin II comprises administering a composition comprising angiotensin II, and the composition further comprises an additional pharmaceutical agent.

19. The method of claim 18, wherein the additional pharmaceutical agent is useful for the treatment of the renal failure associated with cirrhosis.

20. The method of claim 18, wherein the additional pharmaceutical agent is terlipressin, norepinephrine, or midodrine.

* * * * *